(12) United States Patent
Guerguian et al.

(10) Patent No.: US 7,829,008 B2
(45) Date of Patent: *Nov. 9, 2010

(54) FABRICATING A STENT FROM A BLOW MOLDED TUBE

(75) Inventors: Vincent J. Guerguian, San Francisco, CA (US); David C. Gale, San Jose, CA (US); Bin Huang, Pleasanton, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 378 days.

This patent is subject to a terminal disclaimer.

(21) Appl. No.: 11/809,011

(22) Filed: May 30, 2007

(65) Prior Publication Data

US 2008/0300670 A1    Dec. 4, 2008

(51) Int. Cl.
*H05B 6/00* (2006.01)
(52) U.S. Cl. .................. 264/454; 264/535; 264/482; 264/294
(58) Field of Classification Search ................. 623/1.1, 623/1.11, 1.12, 1.13, 1.14, 1.15, 1.16, 1.17, 623/1.18, 1.19, 1.2, 1.21, 1.22, 1.23; 264/239, 264/337, 454, 535, 482, 294
See application file for complete search history.

(56) References Cited

U.S. PATENT DOCUMENTS

| 3,687,135 A | 8/1972 | Stroganov et al. |
|---|---|---|
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,225,109 A * | 9/1980 | Yotsutsuji et al. ........... 249/111 |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,702,884 A * | 10/1987 | Goldstein ..................... 419/8 |

(Continued)

FOREIGN PATENT DOCUMENTS

DE    44 07 079    9/1994

(Continued)

OTHER PUBLICATIONS http://www.engineeringtoolbox.com/thermal-conductivity-d_429.html.*

(Continued)

*Primary Examiner*—Khanh Nguyen
*Assistant Examiner*—Vishal I Patel
(74) *Attorney, Agent, or Firm*—Squire, Sanders & Dempsey, L.L.P.

(57) ABSTRACT

Disclosed is a method for fabricating a stent, the method comprising: positioning a polymeric tube inside a mold, wherein a high thermally conductive element covers at least a portion of the outer surface of the mold, the high thermally conductive element having a thermal conductivity that is greater than that of the mold; heating at least a portion of the mold; radially expanding the tube against the mold; and fabricating a stent from the radially expanded tube.

20 Claims, 3 Drawing Sheets

U.S. PATENT DOCUMENTS

| | | |
|---|---|---|
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,489,405 A * | 2/1996 | Holbert et al. ............... 264/35 |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,891,386 A * | 4/1999 | Deitermann et al. ........ 264/526 |

| Patent No. | Date | Name |
|---|---|---|
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 4,776,337 A | 12/2000 | Palmaz |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,381 B1 | 4/2002 | Hossainy et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,626,939 B1 | 9/2003 | Burnside et al. |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,746,773 B2 | 6/2004 | Llanos et al. |
| 6,752,826 B2 | 6/2004 | Holloway et al. |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,846,323 B2 | 1/2005 | Yip et al. |
| 7,166,099 B2 | 1/2007 | Devens, Jr. |
| 7,666,342 B2 * | 2/2010 | Limon et al. ................. 264/535 |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0103455 A1 * | 8/2002 | Zhang et al. ............. 604/96.01 |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |

| | | | |
|---|---|---|---|
| 2003/0065355 | A1 | 4/2003 | Weber |
| 2003/0093107 | A1 | 5/2003 | Parsonage et al. |
| 2003/0100865 | A1 | 5/2003 | Santini, Jr. et al. |
| 2003/0105518 | A1 | 6/2003 | Dutta |
| 2003/0105530 | A1 | 6/2003 | Pirhonen |
| 2003/0171053 | A1 | 9/2003 | Sanders |
| 2003/0183967 | A1* | 10/2003 | Weber ..................... 264/40.6 |
| 2003/0187495 | A1 | 10/2003 | Cully et al. |
| 2003/0208259 | A1 | 11/2003 | Penhasi |
| 2003/0209835 | A1 | 11/2003 | Chun et al. |
| 2003/0226833 | A1 | 12/2003 | Shapovalov et al. |
| 2003/0236563 | A1 | 12/2003 | Fifer |
| 2004/0093077 | A1 | 5/2004 | White et al. |
| 2004/0098095 | A1 | 5/2004 | Burnside et al. |
| 2004/0111149 | A1 | 6/2004 | Stinson |
| 2004/0127970 | A1 | 7/2004 | Saunders et al. |
| 2004/0143317 | A1 | 7/2004 | Stinson et al. |
| 2004/0167610 | A1 | 8/2004 | Fleming, III |
| 2005/0196485 | A1* | 9/2005 | Cass et al. ................. 425/526 |
| 2006/0076708 | A1* | 4/2006 | Huang et al. ............... 264/239 |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |

OTHER PUBLICATIONS

Acquarulo et al., *Enhancing Medical Device Performance with Nanocomposite Poly*, Med. Device Link, www.devicelink.com/grabber.php3?URL downloaded Mar. 26, 2007, 4 pgs.
Anonymous, *Bioabsorbable stent mounted on a catheter having optical coherence tomography capabilities*, Research Disclosure, Sep. 2004, pp. 1159-1162.
Ansari, *End-to-end tubal anastomosis using an absorbable stent*, Fertility and Sterility, vol. 32(2), pp. 197-201 (Aug. 1979).
Ansari, *Tubal Reanastomosis Using Absorbable Stent*, International Journal of Fertility, vol. 23(4), pp. 242-243 (1978).
Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Devanathan et al., *Polymeric Conformal Coatings for Implantable Electronic Devices*, IEEE Transactions on Biomedical Engineering, vol. BME-27(11), pp. 671-675 (1980).
Elbert et al., *Conjugate Addition Reactions Combined with Free-Radical Cross-Linking for the Design of Materials for Tissue Engineering*, Biomacromolecules, vol. 2, pp. 430-441 (2001).
Hahn et al., *Biocompatibility of Glow-Discharge-Polymerized Films and Vacuum-Deposited Parylene*, J Applied Polymer Sci, vol. 38, pp. 55-64 (1984).
Hahn et al., *Glow Discharge Polymers as Coatings for Implanted Devices*, ISA, pp. 109-111 (1981).
He et al., *Assessment of Tissue Blood Flow Following Small Artery Welding with an Intraluminal Dissolvable Stent*, Microsurgery, vol. 19(3), pp. 148-152 (1999).
Kelley et al., *Totally Resorbable High-Strength Composite Material*, Advances in Biomedical Polymers, vol. 35, pp. 75-85 (1987).
Kubies et al., *Microdomain Structure In polylactide-block-poly(ethylene oxide) copolymer films*, Biomaterials, vol. 21, pp. 529-536 (2000).
Kutryk et al., *Coronary Stenting: Current Perspectives*, a companion to the Handbook of Coronary Stents, pp. 1-16 (1999).
Martin et al., *Enhancing the biological activity of immobilized osteopontin using a type-1 collagen affinity coating*, J. Biomed. Mater. Res., vol. 70A, pp. 10-19 (2004).
Mauduit et al., *Hydrolytic degradation of films prepared from blends of high and low molecular weight poly(DL-lactic acid)s*, J. Biomed. Mater. Res., vol. 30, pp. 201-207 (1996).
Middleton et al., *Synthetic biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., vol. 1(4), pp. 438-448 (Jul./Aug. 1990).
nanoComposix, products, www.nanocomposix.com, downloaded Mar. 26, 2007, 2 pgs.
Nanosiliver, Photocatalyst and Nanocomposite Material, http://eng.nanocomposite.net downloaded Mar. 26, 2007, 1 pg.
Nichols et al., *Electrical Insulation of Implantable Devices by Composite Polymer Coatings*, ISA Transactions, vol. 26(4), pp. 15-18 (1987).
Peuster et al., *A novel approach to temporary stenting: degradable cardiovascular stents produced from corrodible metal-results 6-18 months after implantation into New Zealand white rabbits*, Heart, vol. 86, pp. 563-569 (2001).
Pietrzak et al., *Bioabsorbable Fixation Devices: Status for the Craniomaxillofacial Surgeon*, J. Craniofaxial Surg., vol. 2, pp. 92-96 (1997).
Pietrzak et al., *Bioresorbable implants—practical considerations*, Bone, vol. 19, No. 1, Supplement Jul. 1996, pp. 109S-119S.
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-I-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Völkel et al., *Targeting of immunoliposomes to endothelial cells using a single-chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

* cited by examiner

FABRICATING A STENT FROM A BLOW MOLDED TUBE

BACKGROUND OF THE INVENTION

1. Field of the Invention

This invention relates to methods of fabricating a stent from a blow molded tube.

2. Description of the State of the Art

This invention relates to the fabrication of a stent, from an expanded tube. Stents function to hold open and sometimes expand a segment of a blood vessel or other anatomical lumen such as urinary tracts and bile ducts. Stents are often used in the treatment of atherosclerotic stenosis in blood vessels. A "lumen" refers to a cavity of a tubular organ such as a blood vessel.

A stent has a cylindrical shape and includes a pattern with a number of interconnecting structural elements or struts. Some stents are designed so that they may be radially compressed (crimped) and radially expanded (to allow deployment). A stent can be fabricated from a tube that has been laser cut to form a stent pattern.

The stent must be able to satisfy a number of mechanical requirements. First, the stent must withstand structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity. Once expanded, the stent must adequately maintain its size and shape throughout its service life despite the various forces that may come to bear on it, including cyclic loading, which is induced by a beating heart.

SUMMARY OF THE INVENTION

Various embodiments of the present invention include a method for fabricating a stent, the method comprising: positioning a polymeric tube inside a tubular mold, wherein a high thermally conductive element covers at least a portion of the outer surface of the mold, the high thermally conductive element having a thermal conductivity that is greater than that of the mold; heating at least a portion of the mold; allowing the tube to radially expand within the mold; and fabricating a stent from the radially expanded tube.

Further embodiments of the present invention include a method for fabricating a stent, the method comprising: positioning a polymeric tube inside a mold, the mold having an inner layer and an outer element, wherein the inner layer comprises a glass and the outer element comprises a high thermally conductive material having a thermal conductivity at least 100 times greater than the inner layer; heating at least a portion of the mold; radially expanding the tube against the mold; and fabricating a stent from the radially expanded tube.

BRIEF DESCRIPTION OF THE DRAWINGS

FIG. 3(*b*) depicts a radial, cross sectional view of the blow molding apparatus of FIG. 3(*a*).

DETAILED DESCRIPTION OF THE INVENTION

Various embodiments of the present invention may be applied to stents and, more generally, to implantable medical devices such as, but not limited to, self-expandable stents, balloon-expandable stents, stent-grafts, vascular grafts, or generally, tubular implantable medical devices.

A stent can have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. The present invention is applicable to virtually any stent design and is, therefore, not limited to any particular stent design or pattern. One embodiment of a stent pattern may include cylindrical rings composed of struts. The cylindrical rings may be connected by connecting struts.

In some embodiments, a stent of the present invention may be formed from a tube by laser cutting the pattern of struts in the tube. The stent may also be formed by laser cutting a polymeric sheet, rolling the pattern into the shape of the cylindrical stent, and providing a longitudinal weld to form the stent. Other methods of forming stents are well known and include chemically etching a polymeric sheet and rolling and then welding it to form the stent.

Figure 1:
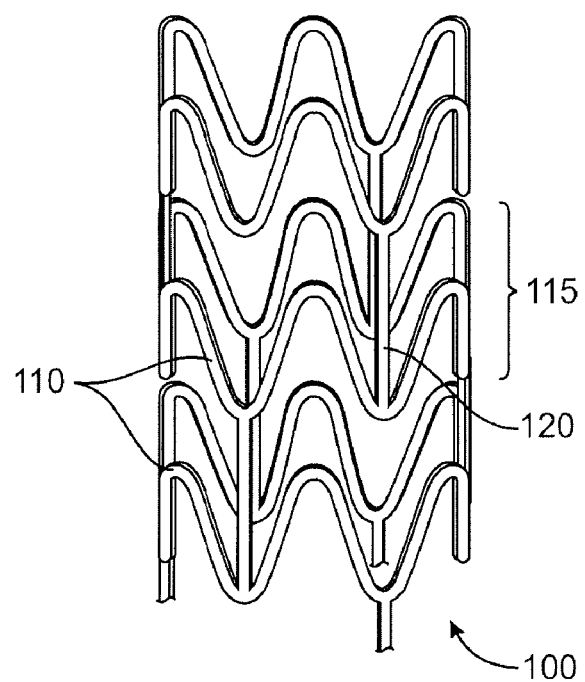
FIG. 1 depicts a stent.

FIG. 1 depicts an exemplary stent 100 with struts 110 that form cylindrical rings 115 which are connected by linking struts 120. The cross-section of the struts in stent 100 is rectangular-shaped. The cross-section of struts is not limited to what has been illustrated, and therefore, other cross-sectional shapes are applicable with embodiments of the present invention. The pattern should not be limited to what has been illustrated as other stent patterns are easily applicable with embodiments of the present invention.

Figure 2:
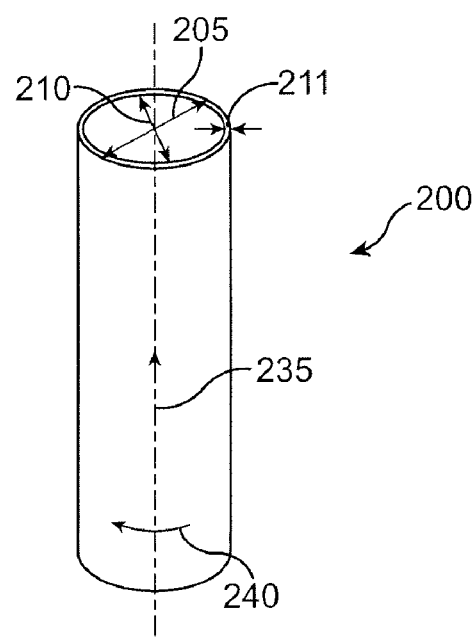
FIG. 2 depicts a polymeric tube for use in fabricating a stent.

As indicated above, it is important for a stent to have high radial strength so that once it is deployed from the crimped state, it can support a lumen. In general, deforming a polymer construct can strengthen the polymer of the construct along an axis of deformation. In some embodiments of fabricating a stent from a polymer tube, the polymer tube can be radially expanded and the stent can be fabricated from the polymer tube in its expanded state. FIG. 2 depicts an exemplary polymer tube 200 for use in forming a stent. Polymer tube 200 has a longitudinal axis 235 and an inner diameter 210 and outer diameter 205 and thickness 211. Polymer tube 200 can be radially deformed by applying stress in the radial direction, which strengthens tube 200 in circumferential direction 240, thereby increasing the tube's radial strength. Strength in the axial direction can also be increased by axial deformation. The uniformity of the radial expansion impacts the concentricity of the expanded tube and the uniformity of expanded thickness 211. These properties are important to the mechanical stability of the stent fabricated from the tube.

The embodiments disclosed herein relate to fabricating a polymeric stent as depicted in FIG. 1 that includes methods for radially expanding a polymeric tube using blow molding. The embodiments of blow molding described herein can increase the uniformity of radial expansion of a tube. As a result, a stent fabricated from the tube has more uniform mechanical properties and greater mechanical stability.

In a blow molding process, a polymer tube is disposed within a mold having an outside diameter that may be a desired expanded diameter of the tube. A radial force is applied to the inside of the tube, typically by blowing a gas into the tube within the mold. A heating nozzle is positioned adjacent to the mold and directs a heated gas at one or more positions on the circumference of the tube. The heated gas flows around and heats the mold and the tube around the circumference. The polymer tube radially expands due to the radial force and the heating.

Whether the mold is heated uniformly depends at least in part on the flow around the circumference and the rate of heat transfer around the circumference of the tube. Typically, a mold is made from a material having a relatively low thermal conductivity, such as glass. Thus, due to inadequate flow of the heated gas and low thermal conductivity, the heat transfer around the circumference of the tube may be inhomogenous or nonuniform which can cause localized hotspots on the tube. Such nonuniform heating can result in nonuniformity of expansion and a lowering of concentricity in the expanded polymeric tube. Concentricity can result in the variation in wall thickness of the expanded tube. Low concentricity and variation in wall thickness is undesirable since a stent requires highly uniform dimensions throughout.

Various embodiments of the present invention relate to methods of blow molding polymer tubes that allow more uniform heating around the circumference of a mold. As a result, the tube is deformed with greater uniformity. A tube that is more uniformly expanded during blow molding allows fabrication of a stent therefrom has more uniform mechanical properties Certain embodiments of the present invention include blow molding with a mold having an inner region or layer and a high thermally conductive material above or over at least a portion of an outside surface of the inner region. The inner region of layer may be a material that is conventionally used in a mold for blow molding, such glass. The high thermally conductive material can have a thermal conductivity that is greater than that of the inner region or layer of the mold. The high thermally conductive material can be selected and positioned in a manner that allows for more uniform heating of the inner region of the mold and polymer tube disposed within during blow molding. The rate of heat transfer in the high thermally conductive material is higher than the inner region or layer of the mold, thereby increasing the rate by which the mold and tube are heated. As a result, localized hot spots in the polymeric tube are reduced or prevented.

In some embodiments, the inner region or layer of the mold can be composed of a material having a relatively low thermal conductivity (k) between 0.1-10 W/m-K. For example, the mold can be glass which as a thermal conductivity of about 1 W/m-K. The high thermally conductive material can have a thermal conductivity that is greater than the inner region or layer of the mold.

The high thermally conductive material may have a thermal conductivity greater than an inner region or layer of a mold. In particular, the high thermally conductive material can have a thermal conductivity that is 2, 20, 50, 100, 200, 300, or more than 400 times that of the inner region or layer of the mold. In exemplary embodiments, the thermal conductivity of the high thermally conductive material can be at least 20, 50, 100, 200, 300, or more than 400 W/m-K. In some embodiments, the high thermally conductive material can be a mold. Exemplary metals include, but are not limited to, aluminum, gold, copper, nickel, steel, stainless steel, oxides of such metals, and alloys and mixtures thereof.

Figure 3A:
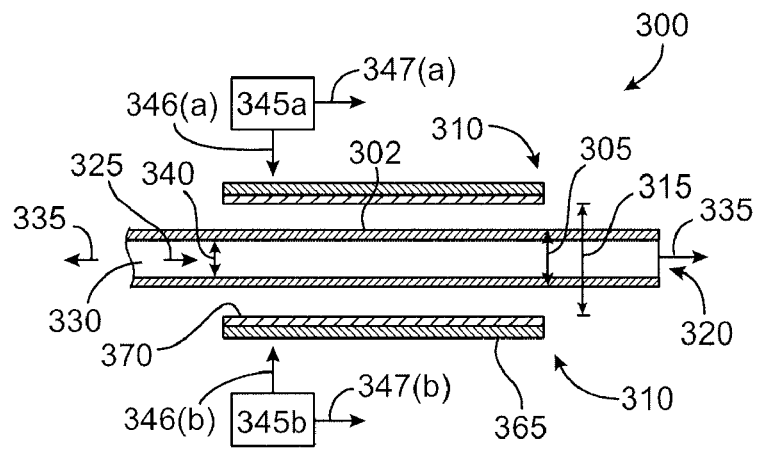
FIG. 3(*a*) depicts an axial, cross sectional view of a blow molding apparatus prior to radially expanding a polymeric tube.
Figure 3B:
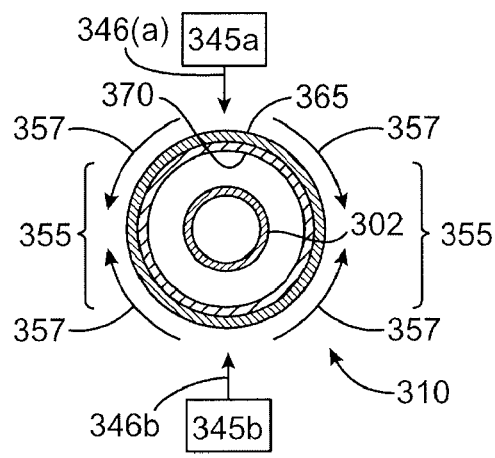
Figure 4:
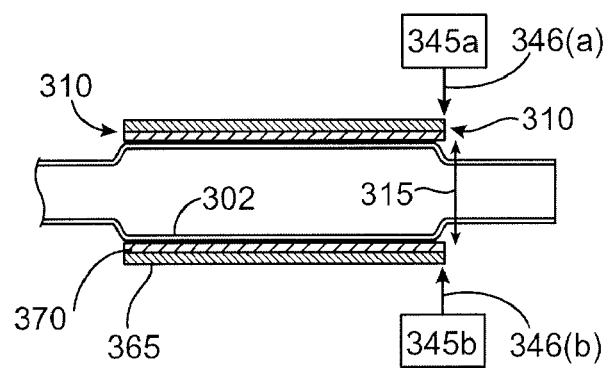
FIG. 4 depicts an axial, cross sectional view of the blow molding apparatus of FIG. 3(*a*) after radially expanding the tube.

FIGS. 3(a)-(b) and 4 depict an illustration of an exemplary blow molding apparatus and method of the present invention. FIG. 3(a) depicts an axial cross-sectional view of a blow molding apparatus with a polymer tube 302 positioned within a tubular mold 310. Polymer tube 302 has an initial outside diameter 305. Mold 310 limits the radial deformation of polymer tube 302 to an outside diameter 315 of mold 310. A nozzle with fluid ports 345a and 345b directs a heated gas, as shown by arrows 346a and 346b, at opposite sides of mold 310.

In one embodiment, mold 310 has an inner layer 370 and a high thermally conductive outer element 365. Inner layer 370 can be formed from a relatively low thermal conductivity material such as glass.

In one embodiment, mold 310 is a two-part mold having an inner layer 370 and an outer layer 365, such that inner layer 370 has good release properties, and the outer layer 365 has a high thermal conductivity. By "release properties", it is meant that a polymer tub can be removed from the blow mold apparatus without substantially cracking the tube.

Outer element 365 can be formed from or include a high thermally conductive material described above that has a higher thermal conductivity than the inner region or layer. Although outer element 365 is shown to completely cover inner layer 370, outer element 365 can be made to only partially cover inner layer 370. As discussed in more detail below, outer element 365 can take the form of a layer, coating, tubular or non-tubular element, wrapping, or other suitable form.

FIG. 3(b) depicts a radial cross-section of apparatus 300 showing polymer tube 302 positioned within mold 310, and heating nozzles 345a and 345b positioned adjacent mold 310. As depicted in FIG. 3(b), mold 310 includes an exterior surface 365 and interior surface 370.

In a blow molding process illustrated in FIG. 3(a), a fluid (conventionally a gas such as air, nitrogen, oxygen, argon, etc.) may be conveyed, as indicated by an arrow 325, into an open proximal end 330 to increase the pressure within polymer tube 302. Polymer tube 302 is closed at a distal end 320, but may be open in subsequent manufacturing steps. For example, the fluid may be conveyed by a nozzle that runs through tube 302. Distal end 320 may be open in subsequent manufacturing steps. Optionally, a tensile force 335 may be applied at proximal end 330 or a distal end 320, or both. The nozzle along with fluid ports 345a and 345b translated axially as shown by arrows 347a and 347b, respectively. As indicated above, a heated stream of gas, as shown by arrows 346a and 346b, is directed on mold 310 and flows around it circumference, also heating regions 355 of the circumference of mold 310 that are not directly impacted by the heated gas stream fluid from ports 345a and 345b. Embodiments of the present invention are not limited to the manner of heating by the heating nozzles illustrated in FIGS. 3(a), 3(b), and FIG. 4.

Polymer tube 302 radially expands, as shown by arrow 340 in FIG. 3(a), as the nozzles 345 and 345 (b) translates axially. The radial deformation is facilitated by the heating by the nozzle and the increase in pressure inside of polymer tube 302. The temperature of the polymer tube can be heated to a temperature above the glass transition temperature (Tg) of the polymer of the tube. FIG. 4 depicts polymer tube 302 in a deformed state with an outside diameter 315 within mold 310.

The outer element 365 has a high thermal conductivity to allow outer element 365 to transfer heat much faster than inner layer 370 around the circumference of polymer tube 302. In particular, heat is transferred at a much higher rate to regions 355 that are away from the direct impact of heated fluid ports 345a and 345b. Thus, heat transferred to outer element 365 can then heat inner layer 370 and polymer tube 302. As a result, outer element 365 allows more uniform heating of inner layer 370 and polymer tube 302 around their circumference. High thermally conductive outer element 365 can reduce or eliminate hot spots that can occur in regions of a mold that are at or near the direct impact of a heated fluid gas stream 346a and 346b. As a result, high thermally conductive outer element 365 can result in a more concentric expanded polymer tube with a smaller variation in thickness around the circumference of the tube.

As discussed above, a mold without high thermally conductive outer element 365 may not be heated with sufficient uniformity by heated gas streams from fluid ports 345a and 345b if inner layer 370 has a relatively low thermal conductivity, for example, that of glass. For such conventional mold materials, the heating of the mold away from the direct impact of a heated gas stream from fluid ports 345a and 345b depends on the flow of heated gas around the circumference and conduction of heat around the circumference. Highly nonuniform heating can result in the formation of hot spots at and near the direct impact of a heated gas streams 346a and 346b.

The thermal conductivity of the high thermally conductive element can be selected to obtain a desired uniformity of heating around the circumference of the mold. In one embodiment, the degree or rate of heat transfer can further be controlled through a thickness of the high thermally conductive element.

Numerous variations of a high thermally conductive element can be used. In certain embodiments, the high thermally conductive element is composed of or includes a highly conductive material such as a metal. In one embodiment, a metal coating can be formed over a surface of a conventional mold. Such a metal coating can be formed by methods known to one of skill in the art such as electroplating, deposition, or thermal spray processing. In another embodiment, metallic particles can be coated, sprayed, or deposited onto the surface of a conventional mold. Other variations of a thermally conductive coating can include highly conductive particles, such as a metal, mixed or dispersed within a binder or adhesive which can be a polymer. Such a coating can be applied onto a surface of a conventional mold by spraying, dipping, or some other manner. The degree of heat transfer can be controlled through the thickness of the element and the concentration of particles in the layer. For example, the layer can have at least 50 wt %, 70 wt %, 90 wt %, or greater than 95 wt % of metal particles in the layer.

In other embodiments, the conductive element can be bonded onto the mold with an adhesive material. For example, a thermally conductive laminate, such as a thermally conductive tape or sticker can be bonded to the mold. The conductive element can also be formed of multiple layers of high thermally conductive material. The conductive layer(s) may be supplied from rolls.

The tubular element can have an inner diameter about the same or slightly larger than the outer diameter of the conventional mold. The tubular element can be composed of or include a highly conductive material. In one embodiment, the tubular element can be a metal tube. Additionally, the tubular element can include highly conductive particles such as a metal, dispersed within a binder. In additional embodiments, the conductive element can be a non-tubular metal sleeve or jacket that is capable of being fitted over a mold.

In some embodiments, the high thermally conductive outer element can be porous. The degree of porosity can be used to control the degree of heat transfer. In one embodiment, the high thermally conductive outer element can be made from a microcellular porous metal. The porosity can be varied, for example, from 0.3 to 1.0. The desired porosity is achievable by a variety of techniques including, but not limited to sintering, foaming, extrusion, thixomolding, semi-solid slurry casting and thermal spraying. The high thermally conductive outer element can be extruded with the inner layer 370.

Additionally, the high thermally conductive outer element can be made from a tubular element of sand metal. The tubular element can be fit over a mold. Sand metal refers to metallic particles bound together through melting the metal particles. Microvoids in the sand metal allow high uniform heat transfer through the tubular element and the mold. Sand metal tubular elements can be formed by methods known in the art such as thermal spray processing. The porosity can be varied to obtain heat transfer properties.

In some embodiments, the high thermally conductive outer element can include two or more sublayers having different thermal conductivities, porosities, or densities. For example, the high thermally conductive outer element can be a metallic tube with metallic particles coated over the surface of the metallic tube.

Figure 5:
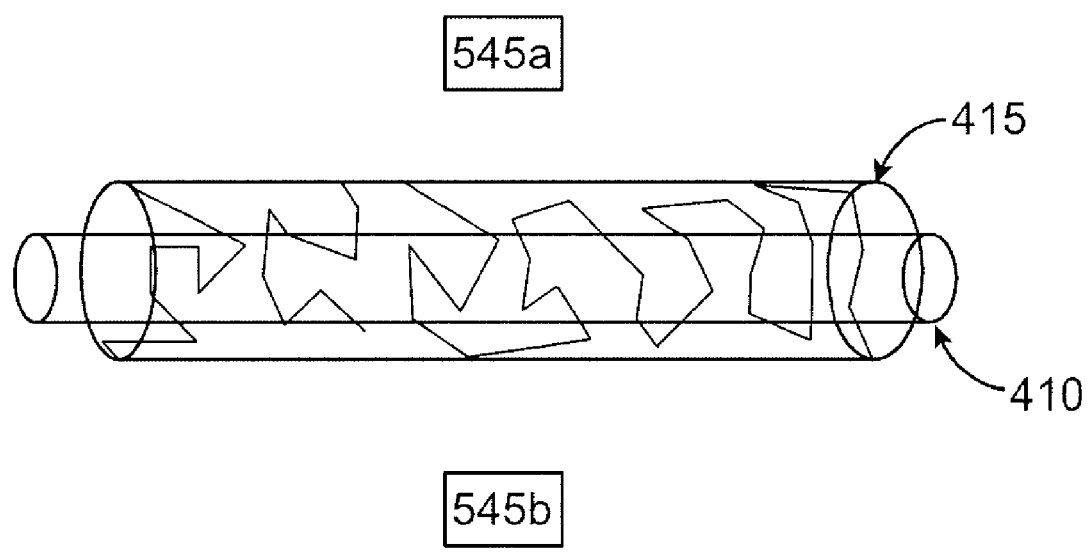
FIG. 5 depicts a side view of a mesh of high thermal conductivity that may be fitted over the exterior of a mold.

In further embodiments, the high thermally conductive outer element can include a metallic mesh that is fitted over a conventional mold to increase the uniformity of expansion. FIG. 5 depicts an exemplary metal mesh 415 disposed over a mold 410, that allows more uniform heating of mold 410 from heated gas streams 346a and 346b from fluid ports 545a and 545b. The degree of heat transfer from the mesh to mold 410 can be controlled through the density of the fibers or wires. The degree of transfer increases the higher the density of the mesh since the greater the surface area of mold 410 that is covered. For example, the mesh can cover at least 10%, 30%, 50%, 70%, or greater than 80% of the surface of mold 410.

In some embodiments, the polymeric tube may be heat set after deformation from the blow molding process to relieve internal stresses within the polymer following deformation. "Heat setting" refers to allowing the polymer construct to equilibrate at a particular configuration at an elevated temperature. The pressure inside the tube, the tension along the cylindrical axis of the tube, and the temperature of the tube may be maintained above ambient levels for a period of time to allow the polymer tube to be heat set. The high thermally conductive element that surrounds the mold can facilitate more uniform heat setting of the tube which can provide more uniform properties through the polymer tube. This can be particularly advantageous for heat setting since wider nozzles can be used in heat setting.

Additionally, the mold having a high thermally conductive element can increase the cooling rate of an expanded polymer tube. Cooling the tube helps insure that the tube maintains the proper shape, size, and length following its formation. Upon cooling, the deformed tube retains the length and shape imposed by an inner surface of the mold. The tube can be cooled slowly or quickly, such as by quenching the tube.

Additionally, a medicated stent may be fabricated by coating the surface of either a metallic or polymeric scaffolding with a polymeric carrier that includes an active or bioactive agent or drug. A polymeric scaffolding may also serve as a carrier of an active agent or drug.

The polymeric tube that is expanded by blow molding can include a biostable biodegradable, or a combination thereof. Polymers can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body.

The processes of breaking down and eventual absorption and elimination of the polymer can be caused by, for example, hydrolysis, metabolic processes, bulk or surface erosion, and the like.

Representative examples of polymers that may be used to fabricate the polymeric tube and stents of the present invention include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen, and hyaluronic acid), polyurethanes, silicones, polyesters, polyolefins, polyisobutylene and ethylene-alphaolefin copolymers, acrylic polymers and copolymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a stent, the method comprising:
   positioning a polymeric tube inside a tubular mold, wherein a high thermally conductive element covers at least a portion of the outer surface of the mold, the high thermally conductive element having a thermal conductivity that is greater than that of the mold;
   heating at least a portion of the mold;
   allowing the tube to radially expand within the mold; and
   fabricating a stent from the radially expanded tube.

2. The method according to claim 1, wherein the high thermally conductive element causes the mold to be heated more uniformly around the circumference of the mold.

3. The method according to claim 1, wherein the high thermally conductive element has a thermal conductivity at least 100 times greater than the mold.

4. The method according to claim 1, wherein the high thermally conductive element comprises a coating over at least a portion of the outside surface of the mold.

5. The method according to claim 1, wherein the high thermally conductive element comprises a metal foil wrapped around the mold.

6. The method according to claim 1, wherein the high thermally conductive element comprises a metallic sleeve that is fitted over the mold.

7. The method according to claim 1, wherein the high thermally conductive element comprises a metallic mesh that is fitted over the mold.

8. The method according to claim 1, wherein the high thermally conductive element comprises a metal selected from the group consisting of copper, gold, and aluminum.

9. The method according to claim 1, wherein a pressured gas conveyed within the polymeric tube and the heating allow the polymeric tube to radially expand.

10. The method according to claim 1, wherein the polymeric tube is heated by a heated gas stream directed at a selected circumferential portion of the mold, the high thermally conductive element facilitating heat transfer to circumferential portions of the mold other than the selected circumferential portions.

11. The method according to claim 1, wherein heating the polymeric tube comprises translating a nozzle axially along the mold, the nozzle directing a heating gas stream to the mold.

12. A method for fabricating a stent, the method comprising:
   positioning a polymeric tube inside a mold, the mold having an inner layer and an outer element, wherein the inner layer comprises a glass and the outer element comprises a high thermally conductive material having a thermal conductivity at least 100 times greater than the inner layer;
   heating at least a portion of the mold;
   radially expanding the tube against the mold; and
   fabricating a stent from the radially expanded tube.

13. The method according to claim 12, wherein the high thermally conductive material increases the uniformity of heating of the inner layer and the polymeric tube around the circumference of the inner layer and the polymeric tube.

14. The method according to claim 12, wherein the high thermally conductive material comprises metal.

15. The method according to claim 12, wherein the high thermally conductive material comprises a material selected from the group consisting of copper, gold, and aluminum.

16. The method according to claim 12, wherein the high thermally conductive material comprises a metal layer that circumvents mold.

17. The method according to claim 12, wherein the high thermally conductive material is bonded to the inner layer.

18. The method according to claim 12, wherein the high thermally conductive material is a layer that is extruded with the inner layer.

19. The method according to claim 12, wherein a pressured gas conveyed within the polymeric tube and the heating allow the polymeric tube to radially expand.

20. The method according to claim 12, wherein the polymeric tube is heated by a heated gas stream directed at a selected circumferential portion of the mold, the high thermally conductive material facilitating heat transfer to circumferential portions of the mold other than the selected circumferential portions.

* * * * *